(12) United States Patent
Cashman et al.

(10) Patent No.: US 7,048,911 B2
(45) Date of Patent: May 23, 2006

(54) UNIT DOSE ORAL TREATMENT PRODUCTS, KITS AND METHODS

(75) Inventors: Stuart Reginald Cashman, Twickenham (GB); Gaelle Moneuze, Egham (GB); Jennifer Claire Morton, Maidenhead (GB); Hai Ye, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 370 days.

(21) Appl. No.: 10/412,085

(22) Filed: Apr. 11, 2003

(65) Prior Publication Data

US 2004/0109830 A1    Jun. 10, 2004

(30) Foreign Application Priority Data

Apr. 12, 2002  (GB) .................................. 0208466

(51) Int. Cl.
*A61K 7/16*   (2006.01)
*A61K 7/20*   (2006.01)
*A61B 19/02*  (2006.01)
*A61B 17/06*  (2006.01)

(52) U.S. Cl. .................. 424/49; 424/53; 206/63.5; 206/438

(58) Field of Classification Search ................ 424/49, 424/53; 206/63.5, 438
See application file for complete search history.

(56) References Cited

U.S. PATENT DOCUMENTS

| | | | |
|---|---|---|---|
| 5,222,813 A | | 6/1993 | Kopp et al. |
| 5,330,747 A | | 7/1994 | Krzysik |
| 5,371,997 A | | 12/1994 | Kopp et al. |
| 5,863,202 A | * | 1/1999 | Fontenot et al. ............. 433/215 |
| 6,113,927 A | * | 9/2000 | Hatakeyama ................ 424/401 |
| 6,569,408 B1 | | 5/2003 | Yue et al. |
| 6,589,512 B1 | * | 7/2003 | Yue et al. ..................... 424/49 |
| 6,649,147 B1 | * | 11/2003 | Ye et al. ....................... 424/49 |
| 6,692,727 B1 | * | 2/2004 | Yue et al. ..................... 424/53 |
| 6,705,467 B1 | * | 3/2004 | Kancsar et al. ............. 206/531 |
| 2003/0203141 A1 | * | 10/2003 | Blum et al. ................ 428/35.7 |
| 2004/0033205 A1 | * | 2/2004 | Date et al. .................... 424/53 |
| 2004/0209974 A1 | * | 10/2004 | Subelka et al. ............. 523/113 |
| 2004/0234792 A1 | * | 11/2004 | Henkens et al. ............ 428/461 |

FOREIGN PATENT DOCUMENTS

| WO | WO 95/01921 A1 | 1/1995 |
|---|---|---|
| WO | WO 01/01940 A1 | 1/2001 |
| WO | WO 02/07636 A1 | 1/2002 |

* cited by examiner

*Primary Examiner*—Raymond J. Henley, III
(74) *Attorney, Agent, or Firm*—Emelyn L. Hiland

(57) ABSTRACT

The present invention provides a unit dose treatment product comprising:
  a) a sealed disposable package comprising a laminate wherein the laminate comprises;
     i) an aluminium barrier layer; and
     ii) a polymer contact layer selected from polypropylene, polyamide and nylon 12;
  b) a liquid treatment product contained within the package, wherein the liquid treatment product comprises:
     i) a film-forming polymer;
     ii) an organic solvent for the film-forming polymer having a boiling point of less than 150° C. and a solubility parameter of less than 22 $(MPa)^{0.5}$; and
     iii) an active agent;
wherein the polymer contact layer of the laminate is in contact with the liquid treatment product.

Kits comprising the unit dose treatment products and methods of treating the tissues of the oral cavity employing the unit dose treatment products are also provided. The products, kits and methods herein provide for convenient oral treatments, especially tooth whitening treatments using an extended regimen.

22 Claims, No Drawings

UNIT DOSE ORAL TREATMENT PRODUCTS, KITS AND METHODS

FIELD OF THE INVENTION

The present invention relates to the packaging and use of oral treatment products comprising volatile solvents for film-forming polymers, particularly wherein the oral treatment products are tooth whitening products.

BACKGROUND OF THE INVENTION

There is a growing demand for people to be able to treat their own teeth, for example with tooth whitening products, beyond the traditional brushing with a cleansing product. An exemplary tooth whitening composition is disclosed in PCT application WO 01/01940.

The treatment fluid disclosed in the above-referenced PCT application is but one example of a number of useful fluid compositions which comprise a film-forming polymer dissolved or dispersed in a volatile solvent which can then be applied, e.g. by painting onto a surface to be treated. One of the problems posed by such fluids is the need to provide a convenient package that prevents the fluid from drying out yet is convenient to use when needed. The applicant has found that further substantial problems are presented by the incompatibility of many common packaging materials with the solvents used. Yet further difficulties are presented by the need to assist the user of such products in sustaining a treatment regimen over a period of several days in an effective and hygienic manner.

It is an object of the present invention, therefore, to provide unit dose treatment products wherein a volatile, film-forming liquid is provided in a convenient package having a prolonged shelf life. It is a further object of the present invention to provide kits containing several such products, together with multiple applicators for the liquid, in order to provide a user in need of such products with an easy to follow regimen which is not halted by clogged or dirty applicators.

These and other objectives will become readily apparent from the detailed description that follows.

All documents cited are, in relevant part, incorporated herein by reference; the citation of any document is not to be construed as an admission that it is prior art with respect to the present invention.

SUMMARY OF THE INVENTION

The present invention provides a unit dose treatment product comprising:
a) a sealed disposable package comprising a laminate wherein the laminate comprises;
  i) an aluminium barrier layer; and
  ii) a polymer contact layer selected from polypropylene, polyamide and nylon 12;
b) a liquid treatment product contained within the package, wherein the liquid treatment product comprises:
  i) a film-forming polymer;
  ii) an organic solvent for the film-forming polymer having a boiling point of less than about 150° C. and a solubility parameter of less than about 22 $(MPa)^{0.5}$; and
  iii) an active agent;

wherein the polymer contact layer of the laminate is in contact with the liquid treatment product. Kits comprising the unit dose treatment products and methods of treating the tissues of the oral cavity employing the unit dose treatment products are also provided.

The products, kits and methods herein provide for convenient oral treatments, especially tooth whitening treatments using an extended regimen.

DETAILED DESCRIPTION OF THE INVENTION

The present invention provides a unit dose treatment product comprising a sealed disposable package and a liquid treatment product contained within the package.

Unless specified otherwise, all percentages and ratios herein are by weight and all measurements are made at 25° C.

The liquid treatment product comprises a film-forming polymer, a solvent for the polymer and an active agent which effects the desired treatment.

Film-Forming Polymer

The term "film-forming polymer" herein means a polymer capable of forming, by itself alone or in the presence of a plasticizing agent, an isolable film. The film-forming polymer can be dissolved, or uniformly dispersed in the form of particles, in the solvent.

The film-forming polymer can include materials such as vinyl polymers; polyurethanes; polyesters; alkyd resins; epoxyester resins; cellulose polymers, such as cellulose esters; modified starches; various silicone materials such as polysiloxanes, silicone gums and resins; and their mixtures. Particularly preferred for use herein are organosiloxane resins.

Organosiloxane resins are highly crosslinked polymeric siloxane systems. The crosslinking is introduced through the incorporation of tri-functional and tetrafunctional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen: silicon atoms is at least about 1.2:1.0.

Silicone materials and silicone resins in particular can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Note that a small amount, up to about 5% of silanol or alkoxy functionality may also be present in the resin structure as a result of processing.

Primes of the unit symbols, e.g., M', D', T', and Q', denote substituents other than methyl, and must be specifically defined for each occurrence. Typical alternate substituents include groups such as vinyl, phenyl, amino, hydroxyl, etc.

The molar ratios of the various units, either in terms of subscripts to the symbols indicating the total number of each type of unit in the silicone, or an average thereof, or as specifically indicated ratios in combination with molecular weight, complete the description of the silicone material under the MDTQ system.

Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The organosiloxane resins are solid at about 25° C. and the average molecular weight of the resins is from about 1,000 to about 10,000. The resins are soluble in organic solvents such as toluene, xylene, isoparaffins, and cyclosiloxanes or the organic solvents described below, indicating that the resin is not sufficiently crosslinked such that the resin is insoluble in the solvent.

The silicone resins preferred for use herein are MQ, MT, MTQ, and MDTQ resins; such MQ resins are disclosed in U.S. Pat. No. 5,330,747, Krzysik, issued Jul. 19, 1994. Thus, the preferred silicone substituent is methyl. Especially preferred are MQ resins wherein the M:Q ratio is from about 0.5:1.0 to about 1.5:1.0. Organosiloxane resins such as these are commercially available, for example, Wacker 803 and 804 available from Wacker Silicones Corporation of Adrian, Mich., US, and G. E. 1170-002 (SR 1000) from the General Electric Company.

The level of the resin that is used in liquid treatment products of the present invention is dependent on its degree of solubility in the formulation, particularly in the solvents used. Generally the range of resin used in the present invention is from about 5% to about 70%, preferably from about 15% to about 45% and most preferably from about 20% to about 40%.

In addition to the organosiloxane resins disclosed above, the liquid treatment products of the present invention may further comprise a fluid diorganopolysiloxane-based polymer to be combined with the organosiloxane resins. Said fluid diorganopolysiloxane-based polymers useful in the present invention span a large range of viscosities; from about 10 to about 10,000,000 $mm^2s^{-1}$ at 25° C. Some diorganopolysiloxane-based polymers useful in this invention exhibit viscosities greater than about 10,000,000 $mm^2s^{-1}$ at 25° C. and therefore are characterized by manufacturer specific penetration testing. Examples of this characterization are GE silicone materials SE 30 and SE 63 with penetration specifications of about 500–1500 and about 250–600 (tenths of a millimeter) respectively.

Among the fluid diorganopolysiloxane polymers of the present invention are diorganopolysiloxane polymers comprising repeating units, where said units correspond to the formula $(R_2SiO)_n$ where R is a monovalent radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof. The fluid diorganopoylsiloxane polymers employed in the present invention may contain one or more of these radicals as substituents on the siloxane polymer backbone.

The fluid diorganopolysiloxane polymers may be terminated by triorganosilyl groups of the formula $(R'_3Si)$ where R' is a monovalent radical selected from the group consisting of radicals containing from 1–6 carbon atoms, hydroxyl groups, alkoxy groups, and mixtures thereof. The fluid diorganopolysiloxane polymer must be compatible in solution with the organosiloxane resin and the volatile carrier. Further description of the organosiloxane resins and fluid diorganopolysiloxane polymers herein is contained in PCT application WO 01/01940.

Solvents

The liquid treatment product further comprises an organic solvent for the film-forming polymer which has a boiling point of less than about 150° C., preferably less than about 100° C., and a solubility parameter of less than about 22 $(MPa)^{0.5}$. Solubility parameters are well known in the art and are readily available from tables, those used herein are SI Hildebrand values from Barton, *Handbook of Solubility Parameters,* CRC Press, 1983.

In the present invention, the film-forming polymer must be easily transferred to a treatment surface, such as tooth enamel. To achieve delivery, it is necessary that the polymers above be incorporated into a solvent, specifically a solvent, which must quickly volatilize, leaving a film containing the active agent.

The organic solvent generally comprises from about 10% to about 90%, preferably from about 15% to about 80%, and more preferably from about 20% to about 70% of the liquid treatment product. The organic solvent is preferably selected from the group consisting of hydrocarbon oils, volatile silicones, non-hydrocarbon solvents, and mixtures thereof.

Hydrocarbon oils useful in the present invention include those having boiling points in the range of about 60 to about 150° C., more preferably hydrocarbon oils having from about $C_6$ to about $C_{10}$ chain lengths, most preferably $C_7$ to $C_{10}$ paraffins and isoparaffins. Most preferred is heptane.

The general classes of non-hydrocarbon solvents useful herein include esters, ketones, alcohols, fluorocarbons and fluorocarbon ethers having boiling points in the range of about 60 to about 150° C. Non-hydrocarbon solvents or mixtures thereof particularly useful include those that are capable of solubilizing the resin and/or the diorganopolysiloxane-based polymer. Such solvents include but are not limited to butanone, ethyl acetate, propyl acetate, amyl acetate, ethyl butyrate, methyl nonafluoroisobutyl ether, methyl nonafluorobutyl ether, and mixtures thereof.

Preferred solvents are those selected from the group consisting of ethyl acetate, 2-butanone and heptane, more preferably 2-butanone (methyl ethyl ketone). Additional solvents may be used as required.

Active Agents

The liquid treatment product further comprises an active agent. A broad range of active agents may be used, subject to compatibility with the polymers and resins herein, including oral and skin care benefit agents.

Most preferred are oral care active agents providing benefits of appearance and structural changes to teeth, whitening, stain bleaching, stain removal, plaque removal, tartar removal, cavity prevention and treatment, inflamed and/or bleeding gums, mucosal wounds, lesions, ulcers, aphthous ulcers, cold sores, tooth abscesses, and the elimination of mouth malodor resulting from the conditions above and other causes such as microbial proliferation.

Suitable active agents include teeth color modifying substances such as pigments; anti-tartar agents, such as polyphosphates; fluoride ion sources such as sodium fluoride; anti-microbial agents such as triclosan; anti-inflammatory agents such as flurbiprofen or naproxen; nutrients such as zinc and vitamins; antioxidants such as ascorbic acid; H2 receptor antagonist compounds such as cimetidine and ranitidine; desensitizing agents such as potassium nitrate; and antiviral actives such as inorganic stannous halides.

A more complete listing of such actives is to be found in PCT publication WO 01/01940.

Other components including flavoring agents, sweetening agents, surfactants, rheology modifiers and chelants may also be included in the liquid treatment products of the present invention.

Preferred active agents are teeth whitening agents that remove or bleach intrinsic or extrinsic stains on or in the tooth surfaces. Such substances are preferably selected from the group consisting of the peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. Suitable metal chlorites include calcium chlorite, barium chlorite, magnesium chlorite, lithium chlorite, sodium chlorite, and potassium chlorite. Additional bleaching substances may be hypochlorite and chlorine dioxide. The preferred chlorite is sodium chlorite. A preferred percarbonate is sodium percarbonate. Preferred persulfates are oxones. The level of these substances is dependent on the available oxygen or chlorine respectively that the molecule is capable of providing to bleach the stain. This level is generally used in compositions of the present invention at levels from about 0.1% to about 35%, preferably from about 1% to about 25% and most preferably from about 5% to about 10% of the liquid treatment product.

Sealed Disposable Package

Another element of the unit dose treatment product herein is a sealed disposable package comprising a laminate. The laminate comprises an aluminium barrier layer and a polymer contact layer selected from polypropylene, polyamide and nylon 12.

The package may comprise any suitable form such as sachets, peelable blisters and tear-open blisters. A preferred packaging form for the disposable package is a three seal sachet having a longitudinal seal and two transverse seals. The three seal sachet is preferably provided with a tear notch extending into one of the transverse seals. PCT application WO 95/01921 describes a suitable three seal sachet. U.S. Pat. Nos. 5,222,813 and 5,371,997 also describe packaging of suitable form. An alternately preferred disposable package form is a peelable blister comprising a tray portion and a cover made from the laminate, the cover being sealed to the tray portion. In such blisters the tray portion is preferably made from the same material as the contact layer of the laminate, most preferably it is polypropylene or has a polypropylene layer in contact with the liquid treatment product. The tray portion can also be formed from the laminate.

The aluminium barrier layer of the laminate is important to prevent escape of solvent and other volatiles from the package. Aluminium by itself is insufficient to form an effective package since it is difficult to seal to itself or to other materials by means of a heat seal. The polymer contact layer performs the function of allowing the package to be conveniently sealed with the liquid treatment product inside it. However, if the integrity of the seal is lost then the package is compromised. For this reason it has been found that the best materials for the polymer contact layer are polypropylene, polyamide and nylon 12. Polypropylene is preferred. Reference to these materials herein also includes copolymers comprising less than about 20%, preferably less than about 10%, more preferably less than about 5% by weight of the polymer of other monomers.

Other materials may be used to construct further layers of the laminate sheet, for example to provide a printable outer surface. These can be any that are customary in the art, such as polyester, polypropylene, polyethylene and polyethylene terephthalate (PET). The layers are adhered to each other as is customary in the art. The thicknesses of the laminate layers are chosen on a combination of tear resistance, cost and barrier function. A suitable laminate for a three seal sachet comprises a 50 μm contact layer of polypropylene adhered to a 20 μm aluminium barrier layer which in turn is adhered to a 12 μm layer of PET which forms an outside layer of the sachet once the sachet is formed.

The package is sized to hold the desired amount of liquid treatment product forming the unit dose, taking into account any headspace desired. Suitable volumes of liquid treatment product are from about 0.1 ml to about 10 mls, preferably from about 0.2 ml to about 2 mls, more preferably from about 0.2 ml to about 1 ml.

Kits

The present invention also provides kits comprising a plurality of the unit dose treatment products and a plurality of applicators. An applicator may comprise a brush having an elongated handle or a replaceable brush portion to be used with a reusable handle. The brush can also be substituted by a sponge or swab. The kit elements may be packaged in a printed outer carton.

A kit preferably comprises one applicator per unit dose product since after use of the applicator it may be clogged by dried treatment product and be unsuitable for re-use. The number of applicators and unit dose products provided in a kit can vary from 10 to 25. In a preferred embodiment a kit contains fourteen applicators and fourteen unit dose products to suit a two week, daily use regimen. The kit may further include a lip retractor as described in PCT publication WO/02/07636 to hold back the lips whilst the liquid treatment product is being applied.

Methods of Use

The invention further relates to a method of treating the soft or hard tissues of the oral cavity comprising: opening the package of a unit dose treatment product as herein described, applying the liquid treatment product to the soft or hard tissues of the oral cavity; and allowing the solvent to evaporate and leaving residual treatment product in contact with the soft or hard tissues of the oral cavity for a treatment period of at least 10 minutes. An additional step of removing residual treatment product at the end of the treatment period may be necessary. For this purpose a toothbrush may also be included in the kit. The treatment period is preferably one hour or more and more preferably overnight.

The method above is intended for an extended regimen and is preferably repeated on a daily basis for a period of seven to twenty-one days, preferably fourteen days. Longer or shorter periods for the regimen may of course be used dependent on the treatment to be applied and the desired effect.

Usage instructions on how to use the kit elements and follow the required regimen should generally also be included in the kit.

EXAMPLE

This is a representative liquid treatment product for use in the present invention. Other representative liquid treatment products are disclosed in PCT publication WO 01/01940.

| Material | % by weight |
| --- | --- |
| Blue pigment, 15% dispersion in polydimethysiloxane | 0.05 |
| SE30[3] premix - 9.76% SE30[3] in DC200/20[1] | 10.25 |
| DC200/12500[1] | 1.0 |
| DC200/20[1] | 9.2 |
| 2-butanone | 3.0 |
| Ethyl acetate | 5.0 |
| MQ resin[2] | 32.5 |
| Flavour | 2.0 |
| Sodium bicarbonate | 8.0 |
| AF230 | 6.5 |
| Fumed silica | 3.5 |
| Sodium Percarbonate | 19.0 |

[1] Polydimethylsiloxanes from Dow Corning
[2] Organosiloxane resin from General Electric
[3] A dimethicone gum from General Electric 0.5 ml of the liquid treatment product is packaged in a sealed three seal sachet to form a unit dose treatment product. The sachet is formed from a laminate comprising a 50 μm contact layer of polypropylene adhered to a 20 μm aluminium barrier layer which in turn is adhered to a 12 μm layer of PET which forms an outside layer of the sachet once the sachet is formed by heat sealing. Fourteen such unit dose treatment products and fourteen brush applicators are enclosed in a carton, thereby forming a kit. The carton further includes usage instructions as follows:

1. Brush teeth and dry teeth.
2. Hold pack upright and tear firmly following line of notch
3. Pick up a drop on your brush (each sachet contains at least ten drops or brush-loads)
4. Apply to teeth
5. Keep mouth open for a 60 seconds to allow the whitening film to form
6. Leave overnight and brush off as normal in the morning Since the invention disclosed herein may be embodied in other specific forms without departing from the general characteristics, the embodiment described herein is, therefore, to be considered in all respects as merely illustrative, the scope of the invention being indicated by the appended claims, rather than by the foregoing description; and all embodiments which come within the meaning and range of equivalency of the claims are therefore intended to be embraced therein.

The invention claimed is:

1. A unit dose treatment product comprising:
    a) a sealed disposable package made from a material comprising a laminate wherein the laminate comprises;
        i) an aluminium barrier layer; and
        ii) a polymer contact layer selected from the group consisting of polypropylene, polyamide and nylon 12;
    b) a liquid treatment product contained within the package, wherein the liquid treatment product comprises:
        i) a film-forming polymer;
        ii) an organic solvent for the film-forming polymer having a boiling point of less than about 150° C. and a solubility parameter of less than about 22 $(MPa)^{0.5}$; and
        iii) an active agent;
    wherein the polymer contact layer of the laminate is in contact with the liquid treatment product.

2. A unit dose treatment product comprising according to claim 1 wherein the polymer contact layer is polypropylene.

3. A unit dose treatment product comprising according to claim 1 wherein the solvent is selected from the group consisting of ethyl acetate, 2-butanone and heptane.

4. A unit dose treatment product comprising according to claim 3 wherein the solvent is 2-butanone.

5. A unit dose treatment product comprising according to claim 1 wherein the film-forming polymer is an organosiloxane resin.

6. A unit dose treatment product comprising according to claim 1 wherein the active agent is a tooth whitening agent.

7. A unit dose treatment product comprising according to claim 6 wherein the tooth whitening agent is sodium percarbonate.

8. A unit dose treatment product according to claim 1 wherein the disposable package is a three seal sachet having a longitudinal seal and two transverse seals.

9. A unit dose treatment product comprising according to claim 8 wherein the sachet includes a tear notch extending into one of the transverse seals.

10. A unit dose treatment product comprising according to claim 1 wherein the disposable package is a peelable blister comprising a tray portion and a cover made from the laminate, the cover being sealed to the tray portion.

11. A unit dose treatment product comprising according to claim 10 wherein the tray portion is formed from polypropylene or has a polypropylene layer in contact with the liquid treatment product.

12. A kit comprising a plurality of treatment products according to claim 1 and a plurality of applicators.

13. A kit according to claim 12 which comprises one applicator per unit dose product.

14. A kit according to claim 12 which further comprises a lip retractor and/or a toothbrush.

15. A kit according to claim 12 which comprises from 10 to 25 applicators and from 10 to 25 unit dose products.

16. A kit according to claim 15 which comprises from fourteen applicators and fourteen unit dose products.

17. A method of treating the soft or hard tissues of the oral cavity comprising:
    a) opening the package of a unit dose treatment product according to claim 1; and
    b) applying the liquid treatment product to the soft or hard tissues of the oral cavity; and
    c) allowing the solvent to evaporate and leaving residual treatment product in contact with the soft or hard tissues of the oral cavity for a treatment period of from about 10 minutes to overnight.

18. A method according to claim 17 which further comprises a step of removing the residual treatment product at the end of the treatment period.

19. A method according to claim 17 wherein the treatment period is about one hour.

20. A method according to claim 18 wherein the treatment period is overnight.

21. A method according to claim 17 wherein steps a) to c) are repeated daily for a period of seven to twenty-one days.

22. A method according to claim 21 wherein steps a) to c) are repeated daily for a period of fourteen days.

* * * * *